US007182951B1

(12) United States Patent
Balachander et al.

(10) Patent No.: US 7,182,951 B1
(45) Date of Patent: Feb. 27, 2007

(54) SELECTION AND TREATMENT OF SEEDS

(75) Inventors: Natarajan Balachander, West Lafayette, IN (US); Julian E. Schafer, Montara, CA (US); Ray F. Stewart, Redwood City, CA (US); David D. Taft, Atherton, CA (US)

(73) Assignee: Landec Corporation, Menlo Park, CA (US)

( * ) Notice: Subject to any disclaimer, the term of this patent is extended or adjusted under 35 U.S.C. 154(b) by 291 days.

(21) Appl. No.: 10/353,848

(22) Filed: Jan. 29, 2003

Related U.S. Application Data

(60) Provisional application No. 60/352,897, filed on Jan. 29, 2002.

(51) Int. Cl.
*A01N 25/00* (2006.01)
*A01N 25/26* (2006.01)
*A01C 1/06* (2006.01)
*A61K 47/30* (2006.01)

(52) U.S. Cl. .................. 424/404; 47/57.6; 504/100; 514/772.3

(58) Field of Classification Search ............... 504/100; 424/404; 47/58, 57.6; 514/772.3
See application file for complete search history.

(56) References Cited

U.S. PATENT DOCUMENTS

| | | | | |
|---|---|---|---|---|
| 3,598,565 A | | 8/1971 | Graves .......................... 71/77 |
| 3,698,133 A | | 10/1972 | Schreiber ..................... 47/57.6 |
| 3,808,740 A | * | 5/1974 | Porter et al. .............. 47/58.1 R |
| 3,947,996 A | * | 4/1976 | Watts .......................... 47/57.6 |
| 4,238,523 A | | 12/1980 | Porter et al. ................... 427/4 |
| 4,251,952 A | | 2/1981 | Porter et al. ................. 47/57.6 |
| 4,272,417 A | | 6/1981 | Barke et al. ................. 260/22 |
| 4,344,979 A | | 8/1982 | Gago ............................ 427/4 |
| 4,380,855 A | | 4/1983 | Deckman et al. ............. 29/407 |
| 4,735,017 A | | 4/1988 | Gago et al. .................. 47/57.6 |
| 4,879,839 A | | 11/1989 | Gago et al. .................. 47/57.6 |
| 5,120,349 A | | 6/1992 | Stewart et al. ................. 71/93 |
| 5,129,180 A | | 7/1992 | Stewart ....................... 47/57.6 |
| 5,156,411 A | | 10/1992 | Owens ....................... 280/79.2 |
| 5,254,354 A | | 10/1993 | Stewart ....................... 426/106 |
| 5,387,450 A | | 2/1995 | Stewart ....................... 428/40 |
| 5,412,035 A | | 5/1995 | Schmitt et al. ............... 525/93 |
| 5,469,869 A | | 11/1995 | Suzuki et al. ................. 131/60 |
| 5,665,822 A | | 9/1997 | Bitlet et al. .................. 525/92 |
| 5,843,982 A | | 12/1998 | Leadbitter ................... 514/422 |
| 5,849,320 A | | 12/1998 | Turnblad et al. ............. 424/410 |
| 5,876,739 A | | 3/1999 | Turnblad et al. ............. 424/408 |
| 6,199,318 B1 | | 3/2001 | Stewart et al. ............... 47/57.6 |
| 6,329,319 B1 | | 12/2001 | Puglisi et al. ................ 504/100 |

OTHER PUBLICATIONS

CAB Abstract, Accession No. 156614 (1995).*
Meulen, V. E. and Henke, F. Cold Testing of Seed Corn Seed World 1948, 63, pp. 8,10.*
Kirkham, M. B. Soil-Water Relationships Encyclopedia of Agricultural Science 1994, 4, pp. 151, 152, 164.*
Article by David Beck entitled Quality Assurance (4 pages) copyright Jul. 23, 2002 on the website of CIMMYT Inc.
Article (anonymous) entitled Go For High Performance With Seed Vigor Tests (2 pages) copyright 1997 ESSO Farm-Tek Advances.
Article (anonymous) entitled Seed Vigor Index (2 pages) published Aug. 9, 2001 (or earlier) by Texas Agricultural Extension Service.
Articles (anonymous) entitled Seed Vigor and Vigor Tests (7 pages) published Aug. 9, 2001 (or earlier) by Ohio State University.
Pittman, Allen et al., *Effect of Polymer Crystallinity on the Wetting Properties of Certain Fluoroalkyl Acrylates,* Journal of Polymer Science, vol. 7, 3053-3066 (1969).
Overberger, C.G., *The Preparation and Polymerization of ρ-Alkylstyrenes. Effect of STructure on the Transition Temperatures of the Polymers,* JACS, vol. 75, 3326-3330 (1953).
Greenberg, Sidney, *Side Chain Crystallization of n-Allkyl Polymethacryslates and Polyacrylates,* JACS, vol. 76, 6280-6285 (1976).
Aharoni, Shaul M., *Rigid Backbone Polymers,* Macromolecules, 94-103 (1979).
Watanabe, Junji, *Thermotropic Polypeptides,* Macromolecules, 18, 2141-2148 (1985).
Rabolt, J.F., *Studies of Chain Conformational Kinetics in Poly(di-n-alkylsilantes) by Spectroscopic Methods,* Macromolecules, 19, 611-616 (1986).
Magagnini, P.L., *Studies on Comb-like Polymers,* Macromolecules, 13, 12-15 (1980).
Yokita, Kenji, *Widely-Spaced Comb-Like Polymers Having Fluoroalkyl Side Chains,* Polymer Journal, vol. 17, No. 9, 9991-996 (19985).
Takayukiootusi, *Effects of Orthoh-Substituents on Reactivities, Tacticities, and Ceiling Temperatures of Radical Polymerizations of Phenyl Methacrylates,* Journal of Polymer Science: Polymer Chemistry Edition, vol. 18, 2197-2207 (1980).
Chupov, V., *Structure and Physico-Chemical Properties of Comb-Like Polypeptides Based on Poly-L-Lysine,* Polymer Science USSR, vol. 21, 241-252.

* cited by examiner

*Primary Examiner*—Johann Richter
*Assistant Examiner*—Ernst Arnold
(74) *Attorney, Agent, or Firm*—Jeffrey G. Sheldon; Sheldon Mak Rose & Anderson P.C.

(57) ABSTRACT

A new vigor test is used to select seeds which, after appropriate polymeric coating, will perform well under adverse planting and growing conditions. For example, suitably coated hybrid corn seeds can be planted earlier than seeds now available, while still obtaining comparable or better yields. Particularly good results are obtained when seeds are coated with compositions comprising a side chain crystalline polymer and an amorphous polymer.

20 Claims, No Drawings

SELECTION AND TREATMENT OF SEEDS

CROSS-REFERENCE TO RELATED APPLICATION

This application is related to, and claims priority from, provisional application No. 60/352,897, filed Jan. 29, 2002. The entire disclosure of that provisional application is incorporated by reference herein for all purposes.

BACKGROUND OF THE INVENTION

1. Field of the Invention

This invention relates to the selection and treatment of seeds, including in particular, but not limited to, hybrid corn seeds.

2. Introduction to the Invention

Yields from seeds depend on the rate and uniformity at which the seeds germinate (as well as other factors such as seed quality, soil quality, the presence of fungi and/or insects, and weather conditions). The rate and uniformity of germination depend on the temperature and moisture content of the soil after the seeds have been planted (as well as other factors). For example, for corn seeds, a soil temperature of 15° C. or higher and a soil moisture content of about 21% are generally regarded as ideal. If the soil temperature and moisture content are too low, germination is poor and nonuniform. If the soil moisture content is satisfactory, but the soil temperature too low, the seeds suffer chilling injury, because they imbibe water which, at the low temperature, causes cell damage. When the soil warms up, germination is poor and nonuniform. In efforts to insure satisfactory germination, farmers generally try to gauge the optimum time for planting, and plant all their seed over a limited time.

It is known to treat seeds with liquid or solid compositions containing active agents which will, directly or indirectly, increase the yield from the seeds. The active agent(s) can for example be applied to the seeds in a liquid composition containing a water-soluble or water-dispersible polymeric binder which, after the composition has solidified, binds the active agent(s) to the seeds. For example, it is common practice, in order to reduce damage by fungi, to treat seeds with compositions containing one or more fungicides. The term "fungicide-treated seeds" is used herein to denote seeds which (i) have a coating thereon comprising a fungicide and binder, the coating being discontinuous and/or the binder being water-soluble or water-dispersible, and (ii) do not have a continuous polymeric coating thereon. It has also been proposed to coat seeds with temperature-sensitive polymers, for example side chain crystalline (SCC) polymers. For further information about known methods of coating seeds, reference to may be made for example to U.S. Pat. No. 3,598,565 (Graves), U.S. Pat. No. 3,698,133 (Schreiber), U.S. Pat. No. 3,808,740 (Porter et al), U.S. Pat. No. 4,238,523 (Porter et al), U.S. Pat. No. 4,251,952 (Porter et al), U.S. Pat. No. 4,272,417 (Barke et al.), U.S. Pat. No. 4,344,979 (Gago), U.S. Pat. No. 4,735,017 (Gago et al), U.S. Pat. No. 4,879,839 (Gago et al), U.S. Pat. No. 5,129,180 (Stewart), U.S. Pat. No. 5,843,982 (Leadbitter), U.S. Pat. No. 5,849,320 (Turnblad et al), U.S. Pat. No. 5,876,739 (Turnblad et al), U.S. Pat. No. 6,199,318 B1 (Stewart et al) and U.S. Pat. No. 6,329,319 B1 (Puglisi et al), the entire disclosures of which are incorporated herein by reference for all purposes.

In order to supply reliable seeds, suppliers of fungicide-treated seeds often subject samples from each seed lot to one or more tests in which the germination percentage is measured under controlled conditions. The seed lots that pass the test(s) are then sold as high-quality seeds. One such test is a "vigor test" which attempts to forecast germination under a range of field conditions. The vigor tests used by different suppliers differ in details, but typically involve determining germination percentages after 7–14 days at 10° C., followed by 7 days at 25° C.

SUMMARY OF THE INVENTION

This invention provides new methods for testing and selecting seeds, new coated seeds, and new compositions suitable for coating seeds. The invention is particularly useful for hybrid corn seeds, but is also useful for other seeds, for example soybean, canola and cotton seeds, as well as other crop seeds.

Some embodiments of the invention make use of a novel vigor test for selecting seeds which will benefit most from appropriate polymeric coatings. Other embodiments of the invention provide seeds having novel polymeric coatings containing fungicides and optionally insecticides. Some preferred embodiments of the invention provide coated seeds, particularly hybrid corn seeds, which have improved resistance to chilling injury. Such seeds can if desired be planted earlier than conventional seeds now available, while still obtaining comparable or better yields. This enables farmers to begin planting earlier (e.g. 2–3 weeks earlier) and/or to plant over a longer period, thus providing flexibility in scheduling, managing, and reducing the cost of, planting equipment and personnel, and reducing the danger that soil conditions will force planting to be unduly delayed.

In a first aspect, this invention provides a method of testing seeds. The method is particularly useful for selecting hybrid corn seeds which will benefit from appropriate polymeric coatings.

In a second aspect, this invention provides coated seeds which carry a continuous polymeric coating and which, before or after being coated, have been tested by the method of the first aspect of the invention.

In a third aspect, this invention provides novel polymeric compositions suitable for coating seeds.

In a fourth aspect, this invention provides coated seeds which carry a coating comprising a composition according to the third aspect of the invention, particularly seeds which, before or after being coated with the composition, were selected by the method of the first aspect of the invention, In a fifth aspect, this invention provides a method of growing crops which comprises planting seeds according to the second and/or fourth aspect of the invention.

The method of the first aspect of the invention tests a seed lot composed of a plurality of seeds, preferably fungicide-treated seeds, including in particular, but not limited to, hybrid corn seeds, which are to be planted in soil. The method comprises the steps of (1) withdrawing a representative sample of seeds from the seed lot;

(2) placing the representative seeds in soil which has a moisture content of M %, where M is 19 to 28%, preferably 21 to 25%, especially about 23%, at a depth of 1–1.5 in. (22.5–38 mm), preferably about 1.25 in. (32 mm);

(3) maintaining the soil and the seeds therein at a temperature of 1 to 10° C., preferably 3 to 7° C., especially about 5° C., for 14 to 28 days, preferably 19 to 24 days, especially about 21 days, while maintaining the moisture content of soil at M %;

(4) immediately after step (3), maintaining the soil and the seeds therein at a temperature of 20 to 30° C., preferably 20 to 25° C., especially about 22° C., while maintaining the moisture content of the soil at L %, where L is 19 to 28%, preferably 21 to 25%, especially about 23%; and (5) determining the percentage of the seeds which have developed into seedlings X days after the beginning of step (4), where X is 7 to 28, preferably 7 to 14, especially on a day at which the maximum number of seedlings can be served.

M is preferably maintained at a substantially constant level. L is preferably maintained at a substantially constant level. L and M are preferably substantially the same. The temperature in step (2) is preferably substantially constant. The temperature in step (3) is preferably substantially constant. The soil in which the seeds of the representative sample are planted is preferably a field soil which is representative of the soil in which the remainder of the seeds are to be planted. The percentages determined in step (5) are of course based on the number of seeds and seedlings, not on their weight.

In one embodiment, the method of the first aspect of the invention is used to test a seed lot in which the seeds are fungicide-treated seeds (as hereinbefore defined). Such seed lots may be seed lots which have been tested by a known vigor test and selected as high-quality seeds. In this embodiment, the test method identifies seed lots which will particularly benefit from additional coating in accordance with the second and/or fourth aspects of the invention. When the percentage determined in step (5) is sufficiently high, for example at least at least 75%, preferably at least 85%, the additional coating provide seeds with improved resistance to cold chill injury. In particular, hybrid corn seeds, after such additional coating, provide good yields even when planted early.

In another embodiment, the test is applied to seed lots which have been coated according to the second and/or fourth aspects of the invention, and when so used can be regarded as a Cold Stress Germination test. Coated seeds according to the second and/or fourth aspects of the invention, when tested by the method of the first aspect of the invention, preferably show a percentage in step (5) of at least 90%, particularly at least 95%.

The compositions of the third aspect of the invention comprise (a) 30 to 95%, preferably 30 to 90%, particularly 40 to 70%, of at least one crystalline polymer, preferably a side chain crystalline (SCC) polymer, especially a polymer which has a peak melting temperature $T_p$ of 0 to 40° C., particularly 0 to 25° C., especially 12 to 25° C., an onset of melting temperature $T_o$ such that ($T_p$–$T_o$) is less than 10° C., and a heat of fusion of at least 5 J/g, preferably at least 15 J/g, for example 5–50 J/g, preferably 20–40 J/g;

(b) 70 to 5%, preferably 70 to 10%, particularly 60 to 30%, of at least one amorphous polymer, preferably an amorphous polymer having a $T_g$ of −60 to 40° C., for example (i) at least one amorphous polymer having a $T_g$ of −40 to 20° C. or (ii) a mixture of at least one amorphous polymer having a $T_g$ of −60 to 40° C. and at least one amorphous polymer having a $T_g$ of 40 to 65° C.; and (c) at least one fungicide, preferably a mixture comprising a contact fungicide and a systemic fungicide.

We theorize that the excellent results provided by the compositions of the third aspect of the invention can be attributed, at least in part, to the following factors. However, the invention is not dependent upon the correctness of our theory.

1. The crystalline component results in a coating whose permeability to water is dependent on temperature. The melting range and the proportion of the crystalline component are chosen so that, at low temperatures, the coating prevents the seeds from imbibing sufficient water to damage the seed. However, the melting range and the proportion are also chosen so that, when the soil temperature rises to a level at which it is desirable for the seed to imbibe water, the transition of at least part of the crystalline component to the amorphous state permits the seed to imbibe water at a controlled and accelerated rate which is desirable for good and rapid germination.

2. The presence of the amorphous polymer makes it easier to apply a consistent and continuous coating on the seeds, and gives the coating greater coherence, hardness and strength, and greater adherence to the seed. As a result, diffusion of the fungicide component (and the optional insecticide component) away from the seed is reduced, and the coating is maintained in close proximity to the seed. This is particularly important in protecting the seed during the critical germination step. If the amorphous polymer is not present, it is more difficult to apply a continuous coating, and the coating is more fragile. As a result, there is a danger that, after the seed has been planted, particularly when the crystalline polymer begins to melt, the coating will fail to prevent fungi and other harmful pathogens (and insects) from contacting the seed.

3. If the soil temperature drops after the seed has begun to imbibe water, the crystalline component returns towards its crystalline state, and the coating inhibits further imbibition, unlike coatings which, for one reason or another, cannot restore their water barrier properties in this way. This process is reversible until the seed has imbibed enough water to start the germination process.

DETAILED DESCRIPTION OF THE INVENTION

In the Summary of the Invention above and in the Detailed Description of the Invention, the Examples, and the claims below, reference is made to particular features (including method steps) of the invention. It is to be understood that the disclosure of the invention in this specification includes all appropriate combinations of such particular features. For example, where a particular feature is disclosed in the context of a particular aspect or embodiment of the invention, or a particular claim, that feature can also be used, to the extent appropriate, in combination with, and/or in the context of, other particular aspects and embodiments of the invention and claims, and in the invention generally.

The term "comprises" is used herein to mean that other ingredients, steps etc. are optionally present. The term "at least" followed by a number is used herein to denote the start of a range beginning with that number (which may be a range having an upper limit or no upper limit, depending on the variable being defined). For example "at least 1" means 1 or more than 1, and "at least 80%" means 80% or more than 80%. The term "at most" followed by a number is used herein to denote the end of a range ending with that number (which may be a range having 1 or 0 as its lower limit, or a range having no lower limit, depending upon the variable being defined). For example, "at most 4" means 4 or less than 4, and "at most 40%" means 40% or less than 40% (including 0%). When, in this specification, a range is given as "(a first number) to (a second number)" or "(a first number)–(a second number)", this means a range whose lower limit is the first number and whose upper limit is the second number. For example, "from 8 to 20 carbon atoms" or "8–20 carbon atoms" means a range whose lower limit is 8 carbon atoms, and whose upper limit is 20 carbon atoms.

Parts and percentages given herein are by weight, except where the context indicates otherwise. For example, where a polymer is said to contain a particular percentage (or range of percentages) of units derived from a particular polymer (or group of polymers), the percentage in question is the percentage by weight of such units, based on the total weight of the polymer. The term "day" is used herein to denote a period of 24 hours.

Tensile Strength and Maximum Elongation values given herein are measured as described in ASTM D-412, at an extension rate of ½ inch per minute, using dumbbell-shaped strips 1 inch long and 3/16 inch wide in the center portion, cut from polymeric films cured at 37° C. The films are 20 mils thick, unless the films are too weak to be tested at this thickness, in which case they are 40 mils thick. The measurements are carried out at 18° C. unless otherwise noted. The Tensile Strength is given in grams. When the film is 40 mils thick, the measured Tensile Strength is divided by 2, for comparability with other Tensile Strength values.

In describing and claiming the invention below, the following abbreviations, definitions, and methods of measurement (in addition to those already given) are used. Parts and percentages are by weight, except where otherwise stated; temperatures are in degrees Centigrade, and molecular weights are weight average molecular weights expressed in Daltons. For crystalline polymers, the abbreviation $T_o$ is used to mean the onset of melting, the abbreviation $T_p$ is used to mean the crystalline melting point, and the abbreviation $\Delta H$ is used to mean the heat of fusion. $T_o$, $T_p$ and $\Delta H$ are measured by means of a differential scanning calorimeter (DSC) at a rate of 5° C./minute and on the second heating cycle. $T_o$ and $T_p$ are measured in the conventional way well known to those skilled in the art. Thus $T_p$ is the temperature at the peak of the DSC curve, and $T_o$ is the temperature at the intersection of the baseline of the DSC peak and the onset line, the onset line being defined as the tangent to the steepest part of the DSC curve below $T_p$. The abbreviation $T_g$ is used to mean glass transition temperature.

Seeds

Fungicide-treated seeds which show germination of at least 85% in one of the known vigor tests are quality seeds which are particularly suitable for use in the various aspects of the invention.

The higher the percentage of the representative seeds which develop into seedlings in step (5) of the test method of the first aspect of the invention, the greater the improvement that can be obtained by coating the remaining seeds in the seed lot in accordance with the second and/or fourth aspects of the invention, and by planting the coated seeds in accordance with the fifth aspect of the invention. When fungicide-treated seeds are tested, the percentage in step (5) will generally be high, and it is preferred to use, in the second, fourth and fifth aspects of the invention, seed lots which, when tested by the test method of the first aspect of the invention, have a percentage in step (5) of the test method of at least 75%, particularly at least 85%. When using seeds which are free of fungicides, the percentage in step (5) will generally be low, and it is preferred to use, in the second, fourth and fifth aspects of the invention, seed lots which have a percentage in step (5) of at least 10%, preferably at least 25%.

Crystalline Polymers

Crystalline polymers, when used in this invention, preferably have a peak melting temperature $T_p$ of 0 to 40° C., particularly 0 to 25° C., especially 12 to 20° C., an onset of melting temperature $T_o$ such that $(T_p-T_o)$ is less than 10° C., and a heat of fusion of at least 5 J/g, preferably least 15 J/g, for example 5–50 J/g, preferably 20–40 J/g. The crystalline polymer can be for example a homopolymer; a random copolymer of one or more monomers; a block copolymer in which one of the blocks is crystalline and the other block(s) is (are) crystalline or amorphous; or a core-shell polymer in which the core is composed of a crystalline polymer and the shell surrounding the crystalline polymer is composed of an amorphous polymer.

The crystalline polymer preferably comprises a side chain crystalline (SCC) polymer, particularly an SCC polymer prepared by emulsion polymerization, especially an emulsion polymer as described in U.S. Pat. No. 6,199,318 B1. SCC polymers are well known, and are described for example in J. Poly. Sci. 60, 19 (1962), J. Poly. Sci. (Polymer Chemistry) 7, 3053 (1969), 9, 1835, 3349, 3351, 3367, 10,1657, 3347, 18, 2197, 19, 1871, J. Poly. Sci., Poly Physics Ed 18 2197 (1980), J. Poly. Sci. Macromol. Rev. 8, 117 (1974), Macromolecules 12, 94 (1979), 13, 12, 15, 18, 2141, 19, 611, JACS 75, 3326 (1953), 76, 6280, Polymer J 17, 991 (1985), Poly. Sci USSR 21, 241 (1979), and U.S. Pat. Nos. 4,380,855, 5,120,349, 5,129,180, 5,156,411, 5,254,354, 5,387,450, 5,412,035, 5,469,869, 5,665,822 and 6,199,318 B1. The disclosure of each of these publications is incorporated herein by reference.

The SCC polymer, or the SCC block of a block copolymer, or the SCC polymer core of a core-shell polymer, can for example contain at least 30%, preferably at least 40%, for example 30–90%, preferably 40–80%, of units derived from at least one n-alkyl acrylate or methacrylate (or equivalent monomer, for example an amide) in which the n-alkyl group contains at least 12, for example 12–50, particularly 12–22, carbon atoms. The other units in the SCC polymers can, for example, be derived from other comonomers containing one or more ethylenic double bonds.

Examples of comonomers containing a single ethylenic double bond include alkyl acrylates and methacrylates (or equivalent monomers, such as amides) in which the alkyl groups (which may be straight or branched chain) contain at most 10 carbon atoms; alkyl acrylates and methacrylates in which the alkyl groups (which may be straight or branched chain) contain at most 10 carbon atoms and are substituted by polar groups, for example hydroxyl or carboxyl groups; acrylic acid; methacrylic acid; and styrene. The percentage of units derived from such monounsaturated comonomers may be at least 10%, for example at least 20%. The percentage of units derived from such comonomers containing polar groups is preferably less than 7%, particularly less than 5%. In a preferred embodiment, the SCC polymer contains at least 20%, e.g. 20–35%, of 2-ethylhexyl acrylate.

The use of comonomers containing two or more, preferably two, ethylenic double bonds produces crosslinked SCC polymers. Cross-linked SCC polymers are often preferred because their use results in coatings which have reduced tack and which may also have improved disintegration characteristics during germination. It is believed that this is because the crosslinking limits the maximum elongation of the coating. The percentage of units derived from such crosslinking comonomers is preferably at most 5%, for example 0.3–3%, preferably 0.7–1.5%. Suitable crosslinking monomers include diacrylates and dimethacrylates, e.g. 1,6-hexanediol diacrylate, tripropyleneglycol diacrylate, 1,3-butyleneglycol dimethacrylate, trimethylolpropane triacrylate and polyethylene glycol 200 diacrylate; divinyl compounds, e.g. divinyl benzene; and diallyl compounds, e.g. dodecanedioic acid diallyl ester.

Crosslinking can also be effected through the use of comonomers having a single ethylenic double bond and another suitable functional group (for example a functional group which reacts when exposed to moisture), for example ethylenically unsaturated silanes such as 3-methacryloxypropyl trimethoxysilane, 3-glycidoxypropyltrimethoxy silane and N-(2-aminoethyl)-3-aminopropyltrimethoxy silane; and TMI (an unsaturated aliphatic monoisocyanate) available than from Cytec, Crosslinking of the SCC polymers can alternatively or additionally be provided by means of a low temperature crosslinking agent which is part of the SCC polymer formulation. Examples of such crosslinking agents include Zinplex 15 (the tradename for a water-soluble complex of zinc oxide in aqueous ammonia available from Ultra Additives), TMXDI (diisocyanate) and XAMA (polyaziridine) available from EIT In one embodiment, the SCC polymer is the core of a core/shell product, preferably of the kind referred to in U.S. Pat. No. 6,199,318 B1. Core/shell products are generally prepared in two stages. The first stage comprises polymerizing the monomers for an SCC polymer, for example a mixture as described above of monomers comprising at least one long chain monomer. The polymerization may take place around a seed polymer, for example an amorphous seed polymer derived from one or more of the comonomers described above, e.g. styrene, 2-ethylhexyl acrylate and methacrylic acid. The second stage comprises polymerizing a second monomer component to form a shell of amorphous polymer around the core of SCC polymer. In one embodiment, the SCC core polymer comprises 60–80% of units derived from at least one n-alkyl acrylate in which the n-alkyl group contains 14–22 carbon atoms, e.g. hexadecyl acrylate; 15–35% of units derived from one or more mono-ethylenically unsaturated comonomers as described above, e.g. 2-ethylhexyl acrylate; and 0.3–2% of a comonomer containing two or more ethylenic double bonds as described above, e.g. 1,6-hexanediol acrylate.

The core preferably provides 10–95%, particularly 50–90%, especially 60–90%, e.g. 60–80%, of the core/shell product, the balance being the non-crystalline shell. The shell is formed by polymerizing the second monomer component. The second monomer component comprises one or more monomers which polymerize to an amorphous polymer, for example one or more of the comonomers described above, e.g. styrene, vinyl acetate or butyl methacrylate. In one embodiment, the shell comprises at least 90% of an acrylate or methacrylate ester, e.g. isobutyl methacrylate; 2–6% acrylic or methacrylic acid; and 0.3–2% of one or more comonomers containing two or more ethylenic double bonds as described above, e.g. 1,6-hexanediol diacrylate.

In one embodiment, the seed polymer, SCC core polymer and amorphous shell polymer, taken together, comprise 45–80% of units derived from at least one n-alkyl acrylate in which the n-alkyl group contains 14–22 carbon atoms, e.g. hexadecyl acrylate, 15–50% of units derived from one or more mono-ethylenically unsaturated comonomers as described above, e.g. one or more of 2-ethylhexyl acrylate, isobutyl methacrylate, acrylic acid and methacrylic acid, and 0.3–2% of one or more comonomers containing two or more ethylenic double bonds as described above, e.g. 1,6-hexanediol diacrylate.

In another embodiment, the SCC polymer is derived from 4–8%, e.g. 6%, styrene-acrylic emulsion polymer (seed), 70–82%, e.g. 75%, alkyl acrylates, 12–20%, e.g. 16%, alkyl methacrylates, 1–4%, e.g. 2%, acrylic acid and/or methacrylic acid, and 0.4–2% or 0.4–1%, e.g. 1%, diacrylate crosslinker.

As noted above, crosslinking of the SCC polymer is desirable to reduce the tack of the polymer. On the other hand, crosslinking reduces the elasticity and elongation of the polymer, and has an adverse effect on the coalescence of the polymer particles, which can lead to coatings having defects and porosity which result in excessive water uptake at low temperatures. Too much crosslinking is, therefore, undesirable. Preferably, the extent of the crosslinking is such that the SCC polymer (whether it is a homopolymer, random copolymer, core-shell polymer, or block copolymer) has a Swelling Ratio (SR) of 10 to 16, preferably 11–14, e.g. 12–13, as defined by the following test. The dried polymer is suspended in an excess of strong solvent e.g. tetrahydrofuran and allowed to equilibrate. The uncrosslinked polymer dissolves in the solvent. The crosslinked polymer absorbs the solvent and swells. The swollen polymer gel is screened from the solvent and weighed. The gel is dried to remove the solvent and weighed again. The Swelling Ratio is the ratio of the weight of the swollen gel to the weight of the dried gel. By using a core-shell polymer, it is possible to make use of an SCC core polymer which has only a small degree of crosslinking, and which therefore has relatively high elasticity and a relatively high Swelling Ratio, for example 16–20. Such an SCC polymer is undesirably soft and tacky if used on its own. However, the amorphous shell around the SCC core polymer makes it possible, for example, to obtain a composite polymer which has a Swelling Ratio of 12–13, but yet has a tack which is substantially less than an unmodified SCC polymer having a much lower Swelling Ratio, for example a Swelling Ratio of less than 9.

Amorphous Polymers

Amorphous polymers, when used in this invention, preferably have a $T_g$ of −60 to 40° C., e.g. −40 to 20° C. An amorphous polymer having a higher $T_g$, e.g. 40–65° C., can be used, preferably in combination with an amorphous polymer of $T_g$ of −60 to 40° C., if a harder coating is desired. Emulsion copolymers are preferred. The amorphous polymers are preferably sufficiently hydrophobic that coatings comprising them limit, but do not prevent, penetration of moisture to the seed. Preferably the amorphous polymer passes the following Water Spot Resistance Test.

An emulsion of the polymer to be tested is drawn down as a wet film onto a sealed black paper test chart (e.g. as available from the Leneta Co.), using a 0.003" (3 mil) Bird film applicator. The film is allowed to dry, either at room temperature or at an elevated temperature which is to be used for coating seeds with the coating formulation (e.g. 30–50° C.). After the chart has been placed in a horizontal position in a temperature-controlled atmosphere at 22° C., 1 ml of deionized water is applied to one spot on the dried film and covered with a watch glass (to prevent water evaporation). The chart is observed for 3 hours. A polymer passes the Water Spot Resistance Test if (a) 30 minutes after the water has been applied, the film does not show any whitening and (b) 3 hours after the water has been applied, the film does not obscure the black test chart, but does show some whitening.

Other significant characteristics of the amorphous polymers are the following.

(1) The minimum film formation temperature (MFFT) influences the ease with which a satisfactory coating is formed on the seeds. In this specification, MFFT values are measured by a Minimum Film Forming Temperature Bar in accordance with ASTM D2354. An MFFT of at most 50° C., preferably at most 30° C., is preferred for this purpose. On the other hand, if the MFFT is too low, the coating may be undesirably tacky. Therefore, an MFFT of at least 5° C., preferably at least 10° C., is preferred. The MFFT of a polymer is related to its $T_g$, but is often lower than $T_g$ when the polymer contains substantial amounts of acid or other hydrophilic groups.

(2) The block resistance of the amorphous polymer influences the tackiness of the coating. A non-tacky coating is highly desirable in order to ensure that the coated seeds are free flowing at room temperature and do not clump and form aggregates or clumps of coated seeds upon storage in about 50 lb sacks, typical for transport of seeds to farmers. This ensures good plantability of the coated seeds through normal seed planters used by farmers. Preferably the block resistance of the polymer is such that paints formulated from the polymer passes the Los Angeles County School District test for overnight block resistance.

(3) The flexibility of the polymer is preferably such that the coating does not crack at temperatures below 10° C.

(4) The elasticity of the polymer is preferably such that the coating does not inhibit swelling of the seed during germination. Therefore, the polymer preferably has a maximum elongation of at least 50%.

(5) The tensile strength of the polymer is preferably high enough that the coating resists abrasion during handling of the coated seeds, but not so high as to retard escape of the first leaves from the seed during germination. Urethane polymers, vinyl chloride copolymers and acrylic polymers in which the average molecular weight of the monomers is less than 100, tend to have a tensile strength which is higher than desirable for this invention.

(6) The polymer emulsion preferably has a small particle size so that the coating formulation dries rapidly into a closely adherent coating. Therefore, a polymer with a median particle size of at most 0.15 micron is preferred.

Satisfactory amorphous polymers can be found, for example, among the acrylic, acrylic/urethane, styrene/acrylic, vinyl acetate/acrylic, vinyl acetate/ethylene, ethylene/vinyl acetate/vinyl chloride, and styrene/butadiene copolymers, particularly styrene/acrylic and other acrylic copolymers. However, depending on the proportion of the amorphous polymer in the coating formulation, many vinyl acetate/acrylic copolymers, vinyl acetate/ethylene copolymers, and acrylic/urethane polymers are sufficiently hydrophilic to give rise to coatings which are undesirably permeable to water, as also are many commercially available styrene/butadiene latex polymers because they contain high levels of surfactant. Conversely, and again depending on the proportion of the amorphous polymer, vinylidene chloride polymers and polymers containing too much styrene (for example more than 25%) tend to give rise to coatings which are insufficiently permeable to water. Examples of suitable commercially available acrylic emulsion polymers are Rhoplex SG20 and SG10 available from Rohm & Haas, and Acronal Optive 100, 110 and 310 available from BASF. Examples of commercially available acrylic/urethane polymers are Flexthane 620 and 630 available from Air Products.

Coating Formulations

As noted previously, it is known to coat seeds with fungicidal coatings which are based on water-soluble or water-dispersible polymers or binders. These polymers or binders not only provide a way to apply the fungicide to the seeds, but also minimize dusting of the toxic fungicide material when seeds are transferred from bags to seed planters by farmers. Surprisingly, we have found that, contrary to the accepted practice of using water-soluble or water-dispersible binders to hold the fungicide to the seed, improved results are obtained if the fungicidal coating has limited water sensitivity. We theorize that the known water-soluble or water-dispersible coatings dissolve and/or disintegrate in moist soil, even at water contents below those needed for germination. This causes the fungicides to migrate into the soil away from seeds, thus reducing the fungicide concentration around the seeds at a particularly critical time, namely while they are germinating. The use of coatings of greater hydrophobicity (particularly those whose water sensitivity undergoes a sharp increase at desired germination temperatures) results in a higher concentration of fungicides at this critical time.

The polymer in the seed coating formulations used in this invention can consist of at least one crystalline polymer, at least one amorphous polymer, or, preferably, a blend of at least one crystalline polymer and at least one amorphous polymer. Whichever of these alternatives is used, the polymer or polymers should be selected with the objective of achieving a coating formulation which can be easily applied to seeds to form a fast-drying coating and which, after drying, forms a coherent, non-tacky coating which has satisfactory water permeability. We have found that such coatings are generally most easily achieved when the polymeric component of the coating composition has a maximum elongation of 100 to 250%, preferably 125 to 200%, and a tensile strength of 400 to 3000 grams, preferably 800 to 1700 grams. Crystalline polymers, when used alone, can provide excellent water permeability characteristics, in particular a rapid transition from limited permeability at temperatures below the desired germination temperature to increased permeability at higher temperatures. However, the crystalline polymers can be difficult to apply, and they tend to form coatings which are undesirably tacky, so that the coated seeds stick together and are difficult to plant. As noted previously, this problem can be reduced by crosslinking. Amorphous polymers, when used alone, can provide excellent coatings, but not the rapid transition in water permeability which can be obtained with crystalline polymers.

We have found that the desired objectives can be most closely approached when a blend of crystalline and amorphous polymers is used. However, improved results can be obtained when only crystalline polymers or only amorphous polymers are used. At present, suitable crystalline polymers are generally less readily available and more expensive than suitable amorphous polymers. Therefore, cost considerations may make it commercially desirable to use formulations which contain only amorphous polymers, even though the early planting capability of the coating seeds is less satisfactory than can be achieved when using blends of crystalline and amorphous polymers.

When, as is preferred, the coating compositions contains a blend of at least one crystalline polymer and at least one amorphous polymer, the polymers are preferably compatible with each other. The term "compatible" is used herein, in relation to a blend of polymers, to mean that the blend passes the following Compatibility Test.

Emulsions of the polymers to be tested are blended together in the desired ratio. The blend is drawn down as a wet film onto a sealed black paper test chart (e.g. as available from the Leneta Co.), using a 0.003" (3 mil) Bird film applicator, and the film is allowed to dry under the conditions to be used to dry the coating formulation on the seeds. The polymers pass the Compatibility Test if the dried film is transparent so that the black chart can be seen without haziness or obscurity through the dried film.

Preferred coating compositions comprise
  (a) 30 to 95%, preferably 30 to 90%, particularly 40 to 70%, of at least one crystalline polymer, preferably a side chain crystalline polymer, especially a polymer which has a peak melting temperature $T_p$ of −5 to 50° C., preferably 0 to 40° C., particularly 0 to 25° C., especially 12 to 20° C., an onset of melting temperature $T_o$ such that $(T_p-T_o)$ is less than 10° C., and a heat of fusion of at least 5 J/g, preferably least 15 J/g, for example 5–50 J/g, preferably 20–40 J/g; and
  (b) 70 to 5%, preferably 70 to 10%, particularly 60 to 30%, of at least one amorphous polymer, preferably an amorphous polymer having a $T_g$ of −60 to 40° C., for example (i) at least one amorphous polymer having a $T_g$ of −40 to 20° C. or (ii) a mixture of at least one amorphous polymer having a $T_g$ of −60 to 40° C. and at least one amorphous polymer having a $T_g$ of 40 to 65° C.

Fungicides

Fungicides which can be used in this invention are well known. Often a mixture of fungicides, e.g. a mixture of at least one contact fungicide and least one systemic fungicide is used. Preferably at least some of the fungicide is incorporated into a polymeric coating composition, particularly a coating composition containing an SCC polymer and/or an amorphous polymer. However, it is alternatively or additionally possible to apply some or all of at least one fungicide directly to the seed and/or to the exterior of the polymeric coating on a coated seed. The fungicides are often used in combination with inert ingredients, wetting agents, and other additives. The concentration of the fungicide or mixture of fungicides can for example be from 25 to 10,000 ppm, but is generally less than 3000 ppm, for example 25 to 2000 ppm, preferably 1200 to 1600 ppm, based on the weight of the seed. When a mixture of fungicides is used, preferably the concentration of each of the fungicides is 20 to 1000 ppm, based on the weight of the seed.

Preferred fungicides include trichloromethylthiocyclohexene-1,2-dicarboximides, e.g. N-trichloromethylthio-4-cylcohexene-1,2-dicarboximide, which is available from Gustafson under the trade name Captan; N-(methoxyacetyl) alanine esters, e.g. N-(2,6-dimethyl)-N-methoxyacetyl)d,l-alanine methyl ester, also known as Metalaxyl, which is available from Gustafson under the tradename Allegiance and from Syngenta under the tradename Apron XL; bis-dialkylthiocarbamoyl disulfides, for example bis-(dimethylthiocarbamoyl) disulfide, which is available from Gustafson under the tradename Thiram; and difluorobenzodioxolyl pyrrole carbonitriles, e.g. 4-(2,2-difluoro-1,3-benzodioxol-4-yl)-1H-pyrrole-3-carbonitrile, also known as Fludioxonil, which is available from Novartis under the tradename Maxim. A fungicide of the Apron type is particularly important for early-planted corn seed as it protects against common early spring soil born diseases caused by phytopthora and pythium. Many of these fungicides are used or supplied as mixtures. For example, a mixture of Captan and pentachloronitrobenzene is available from Gustafson under the tradename Rival; Maxim and Apron are often used in combination as a corn fungicide; and Captan, Apron and Thiram are often used together. Apron is a systemic fungicide while many of the other fungicides mentioned, e.g. Captan and Thiram are contact fungicides. In the tables below, the abbreviations C, A and T are used for the fungicides Captan, Apron and Thiram respectively.

Preferred fungicides for use in this invention are mixtures of Captan (e.g. in amount 300 to 750 ppm), Apron (e.g. in amount 25 to 100 ppm) and Thiram (e.g. in amount 200 to 800 ppm; and mixtures of Apron (e.g. in amount 25 to 100 ppm) and Maxim (e.g. in amount 25 to 50 ppm).

Insecticides

Insecticides which can be used in this invention are well known. They provide protection against, for example, wireworms and corn root worms. Commercially available insecticides include those available under the tradenames Gaucho, Lorsban and Force. A preferred insecticide for use in this invention is 1-[(6chloro-3-pyridinyl)methyl]-N-nitro-2-imidazolidinimine, also known as Imidacloprid, which is available from Gustafson under the tradename Gaucho. Lorsban is o,o-diethyl-o-(3,5,6-trichloro-2-pyridyl)phosphorothioate.

Other Ingredients

Other ingredients can be present in the coating to assist in its application to the seeds or its properties after it has been applied. Such other ingredients include wetting agents, slip agents, hardening agents, and fillers. It is also possible to apply other ingredients during or after the application and drying steps, for example to reduce the tack and to improve the surface slip of the coated seeds.

Application of the Polymeric Coatings

Methods for applying polymeric coatings to seeds are well known to those skilled in the art. In this invention, the polymer is preferably in the form of an emulsion when it is applied to the seeds. For details of the preparation and properties of emulsions of SCC polymers, and their application to seeds, reference may be made to U.S. Pat. No. 6,199,318 B1 (Stewart et al), the disclosure of which is incorporated herein by reference. As noted above, the polymeric coating preferably contains one or more fungicides, preferably distributed uniformly in the polymeric coating. The polymeric coating can also contain one or more fillers, for example up to 50% of the total coating weight. The weight of the dried coating can be for example) 0.5–4%, preferably 1–3.4%, particularly 1.5–3%, especially 1.2–1.9%, based on the weight of the seed.

Heat Unit Delay

This invention includes coated seeds which are particularly valuable because they can be planted early. However, it is possible, for example because the weather conditions do not permit early planting, that such seeds will in fact be planted at normal planting time or late. If this happens, some of the polymeric coatings which are valuable in protecting the seeds from early cold stress may cause an undesirable delay in germination, resulting in relatively poor yields at normal harvest time. We have found that, in order to reduce this danger of undesirable delay in germination, the coated seeds should have a relatively low Heat Unit Delay, preferably a Heat Unit Delay of less than 50, particularly less than 30.

The Heat Unit Delay of seeds is a measure of the amount of additional heat needed to cause the coated seeds to germinate and grow, by comparison with uncoated seeds, and in this specification is measured using the Warm Germination Test described below. In the Warm Germination Test, 21.6 Heat Units are input to the seeds each day. 21.6 is the difference between the test temperature in ° F. (71.6) and 50° F., which is chosen on the assumption that temperatures less than 50° F. do not contribute to significant growth of the seedlings. If, therefore, the coated seeds take P days longer to germinate than the uncoated seeds, the Heat Unit Delay of the coated seeds is 21.6P.

EXAMPLES

The invention is illustrated by the following Examples. In the Examples, the following abbreviations, equipment, materials, coating methods and tests were employed.

Acronol Optive-100 is an acrylic emulsion available from BASF

Acrysol RM12 W is a rheology modifier available from Rohm & Haas

Albaglos is calcium carbonate, 0.6 microns, available from Specialty Minerals

KTPP is potassium tri-polyphosphate

BYK022 is a defoaming agent available from Byk Chemie, and is believed to be a mixture of polydimethyl siloxanes, polyglycols, hydrophobic silica and surfactants BYK156 is a pigment dispersant available from Byk Chemie, and is believed to be an aqueous solution of an acrylic acid copolymer ammonium salt BYK333 is an anti-slip agent available from Byk Chemie, and is believed to be a polyether modified polydimethyl siloxane BYK345 is a wetting agent available from Byk Chemie, and is believed to be a polyether modified polydimethyl siloxane C3-A is an emulsion of a core-shell SCC polymer (47% solids) dispersed in a mixture of water and n-propanol. The polymer has a $T_p$ of 19–21° C. The crystalline core is composed of units derived from 69.8% n-hexadecyl acrylate, 27.5% 2-ethylhexyl acrylate, 2.0% methacrylic acid and 0.7% 1,6-hexanediol diacrylate. The shell is composed of 69.8% isobutyl methacrylate, 27.5% 2-ethylhexyl acrylate, 2.0% methacrylic acid and 0.7% 1,6-hexanediol diacrylate D1-G polymer is an emulsion of an SCC polymer (43% solids) dispersed in a mixture of water and n-propanol. The polymer has a $T_p$ of 19–21° C., and is composed of units derived from 65.8% n-hexadecyl acrylate, 24.3% n-hexyl acrylate, 3.9% styrene, 4.3% methacrylic acid, 1.1% 2-ethylhexyl acrylate and 0.6% 1,6-hexanediol diacrylate.

D3-J polymer is an emulsion of an SCC polymer (43% solids) dispersed in a mixture of water and n-propanol. The polymer has a $T_p$ of 19–21° C., and is composed of units derived from 66.0% n-hexadecyl acrylate, 25.0% 2-ethylhexyl acrylate, 3.9% styrene, 4.3% methacrylic acid, and 0.8% 1,6-hexanediol diacrylate FC 8083, FC 8088, FC 8288, FC 8409, FC 8411, FC 8417, FC 8809, FC 9114, FC 9301 and FC 9307 are lots of hybrid corn seed available from Fielder's Choice Flexbond 825 is available from Air Products and Chemicals Inc and is believed to be a vinyl-acrylic copolymer Lubracal is a lubricant designed for paper milling, available from Witco Corp., and is believed to be a 48% dispersion of calcium stearate powder in water, with other soaps Mowiol 4-88 is available from Clariant Corp. and is believed to be a water-soluble polymer of vinyl alcohol prepared by hydrolysis of polyvinyl acetate Makon NP-10 is a non-ionic surfactant available from Stepan Chemical, and is believed to be a nonylphenol ethoxylate Methocel J20MS is a thickener available from Dow Chemical Corp. and is believed to be a surface-treated hydroxypropyl methylcellulose polymer Optigel WA is a clay-based thickener available from United Catalysts, and is believed to be an amine-treated bentonite Raykote 1486 is an amorphous polymer available from Specialty Polymers and is believed to be a styrene-acrylic emulsion polymer Rhoplex SG20 is a polymer available from Rohm & Haas Co., designed for formulating gloss emulsion paints with good block resistance, and is believed to be an acrylic emulsion Seed Colorant is available from Loveland Industries under the tradename Seed Mate Seed Colorant, and is believed to be a rhodamine pigment-based seed colorant.

Tegoglide 450 is a mar and slip additive available from Tego Chemie, and is believed to be a polyether-modified polydimethyl siloxane Tergitol 15S40 is a non-ionic surfactant available from Union Carbide, and is believed to be a secondary alcohol ethoxylate Zinplex 15 is an external crosslinker available from Ultra Additives.

Diamond Coater

The Diamond Coater was manufactured by Diamond Coating Co. of Arizona under the tradename Diamond L Coater. It comprises a perforated coating pan which is fitted with baffles and is capable of handling 5–20 lb (2–10 kg) of seeds per batch. The coating formulation is applied to the seeds in the pan through spray nozzles above the pan while the pan is rotated and while hot air is circulated. Moist air is exhausted through a particulate filter. Typically, the pan is rotated at 11 rpm, the pump speed is 60 mL/min, and the coating time is 10–20 minutes depending on the desired coating weight.

ETS R-12 Coater

The ETS R-12 Coater was manufactured by ETS Systems of California. It comprises a rotostat and an atomizer shaft. The coating formulation was added to the atomizer by a peristaltic pump and atomized onto the seeds spinning on the coater. Typically, the addition time was about 8 seconds. The coated seeds were discharged to a destoner dryer (manufactured by Forsberg of Minnesota) maintained at 60° C. If further coating was required, the dried seeds were returned to the coater. Typically, two or three passes through the coater were needed to achieve the desired coating weight.

Polymer Only Coating Method, and Fungicide in Polymer Coating Method

About 10 lb (4.5 kg) of seed was placed in the pan of the Diamond Coater. The coating formulation, containing a polymer and, in some cases, one or more fungicides, was pumped into the coater at a rate of 60 mL/min, with continuous drying.

Overcoat Method

The Overcoat Formulation H was applied to the seeds in the pan of the Diamond Coater, and the seeds were then dried. The overcoat formulation was applied to provide a non-functional dry and mechanically hard coating.

Fungicide Under Coating Method

About 5 lb (2.25 kg) of seed was placed in the pan of an ETS-R12 rotostat coater. Half the fungicide mixture was applied to the seeds and mixed for 15 seconds. The fungicide mixture was obtained by mixing commercially available fungicides slurries. The seeds were removed and dried on the dryer. A second batch of seeds was coated in the same way. The two batches were combined. The combined batches were coated by the Polymer Only Coating Method, or Fungicide in Polymer Coating Method Coating Formulations The coating formulations used in the Examples were prepared as follows.

Formulation A

Formulation A was a pigment grind used as a seed colorant in Formulation B described below. The mixing tank of a Cowles mixer was charged with water (800 g) and a mixture of Methocel J20MS (7.5 g) and propylene glycol (19.9 g).

After the agitator had been turned on, BYK022 (2.0 g), KTPP (2.4 g), Makon NP-10 (3.0 g) and BYK156 (18.2 g) were added. Then Albaglos (2000 g) was added in small quantities, each of which was incorporated before the next was added. The pigment grind increased in temperature and became thinner above 105° F. (40° C.). A mixture of Optigel WA (3.0 g) and water (30 g) was added all at once and agitation was continued until the temperature in the tank rose to 120° F. (49° C.). The disperser was then shut off, and the pigment grind drained into containers.

Formulation B

Formulation B contained a crosslinked SCC polymer emulsion and a styrene-acrylic polymer emulsion. Water (125 g) and D1-G polymer (368 g, 42.8% solids) were mixed in a mixing tank, and BYK022 (0.04 g) and a 50% aqueous solution of Tergitol 15S40 (4.5 g) were then added. A solution of Zinplex 15 (20.4 g) and water (100 g) was slowly pumped into the resulting polymer latex over a period of 5 minutes. After mixing for an additional 5 minutes, Rayokote-M1486 (143.6 g) and Formulation A (106 g) were added sequentially. A mixture of BYK333 (1.12 g) and BYK345 (1.12 g) in water (20 g) was then added to the mixing tank. Formulation A (2 g) and a mixture of Acrysol RM12 W (0.57 g), water (2.0 g) and n-propanol (2.0 g) were then added. Formulation B was diluted with water as required.

Formulation C

Formulation C contained a crosslinked SCC polymer emulsion and an acrylic polymer emulsion. D3J polymer latex (425 g, 46.3% solids) was placed in a mixing vessel. To it was added a mixture of water (29 g), 50% Tergitol 15S40 solution (7.9 g), Tegoglide 450 (2.0 g) and BYK345 (3.9 g). A mixture of Zinplex15 (27.8 g) and water (929 g) was then added over a period of 5 minutes. Rhoplex SG20 (429.6 g), Lubracal 48 (40.3 g) and Seed Colorant (5.8 g) were then added. The resulting mixture was diluted to 35% solids by adding water.

Formulation D

Formulation D contained a crosslinked SCC polymer emulsion, a styrene-acrylic polymer emulsion, and an acrylic polymer emulsion. D3J polymer latex (125.8 g, 46.3% solids) was placed in a mixing vessel. To it was added a mixture of water (910 g), 50% Tergitol 15S40 solution (2.7 g), Tegoglide 450 (0.65 g) and BYK345 (1.35 g). A mixture of Zinplex15 (27.8 g) and water (929 g) was added slowly. Rhoplex SG20 (103.3 g), Rayokote M1486 (44.5 g) and Seed Colorant (2.0 g) were then added. The resulting mixture was diluted to 35% solids by adding water.

Formulation E

Formulation E contained a crosslinked SCC polymer core/shell emulsion and an acrylic polymer emulsion. C3-A core-shell polymer (70.5 g, 47.9% solids) was mixed with a solution of Tegoglide 450 (1.41 g) and BYK345 (2.82 g) in water. A solution of Zinplex15 (3.95 g) in water (8.0 g) was added slowly. Acronol Optive-100 (45.0 g) and Seed Colorant (1.80 g) were then added sequentially). The resulting mixture was diluted to 35% solids by adding water.

Formulation F

Formulation F contained an acrylic polymer emulsion. Rhoplex SG20 (430 g) was mixed with a solution of Tegoglide450 (0.98 g) and BYK 345 (1.96 g) in water (29 g). The resulting mixture was diluted to 35% solids by adding water.

Formulation G

Formulation G contained a crosslinked SCC polymer core/shell emulsion and an acrylic polymer emulsion. C3-A core-shell polymer (1440 g, 47% solids) was mixed with a solution of Tegoglide 450 (28.2 g, 20% solids) and BYK345 (56.4 g, 20% solids) in water (50 g). A solution of Zinplex15 (79 g) in water (160 g) was added slowly. Acronol Optive-100 (900 g, 25% solids) and Seed Colorant (36 g) were then added sequentially. The resulting mixture was diluted to 35% solids by adding water.

Formulation H

Formulation H was the overcoat formulation. Water (204 g), Flexbond 825 (82.4 g) and 15% Mowiol 4-88 solution in water (103.8 g) were mixed together. To the resulting mixture were added a mixture of BYK333 (0.7 g) in water (1.5 g) and a mixture of Seed Colorant (0.2 g) and water (1 g).

Vigor Test

A 0.5 in. (12.5 mm) thick layer of field soil having a moisture content of 20% was placed in a plastic tray 10×2×2 in. (250×50×50 mm). Fifty (50) seeds were withdrawn from a seed lot and placed uniformly on top of the layer of soil. Additional field soil having a moisture content of 20% was added to cover the seeds so that the total thickness of the soil in the tray was about 1.75 in. (44.5 mm) and the total weight of the tray was about 1000 g. Additional water was added to the soil until it had a moisture content of 23%. The tray was immediately placed in a chamber maintained at 5° C. After 21 days in the chamber at 5° C., the tray was placed in a chamber maintained at 22° C. The emerging seedlings were counted each day until the maximum stand count had been reached. Throughout the test, water was added to the soil whenever necessary to maintain its moisture content at 23%.

Table 1 below sets out the results of applying the Vigor Test to a number of different varieties of hybrid corn seed available from Fielder's Choice under the tradenames shown in the Table.

TABLE 1

| Example | 1 | 2 | 3 | 4 | 5 | 6 | 7 | 8 | 9 | 10 |
|---|---|---|---|---|---|---|---|---|---|---|
| Variety FC | 8417 | 9307 | 8411 | 8409 | 9114 | 8083 | 8809 | 9301 | 8088 | 8288 |
| % germination | 26 | 41 | 46 | 63 | 89 | 35 | 88 | 91 | 82 | 78 |

Warm Germination Test

A 0.5 in. (12.5 mm) thick layer of field soil having a known moisture content was placed in a plastic tray 10×2×2 in. (250×50×50 mm). Fifty (50) seeds were withdrawn from a seed lot and placed uniformly on top of the layer of soil. Additional field soil having the same moisture content was added to cover the seeds so that the total thickness of the soil in the tray was about 1.75 in. (44.5 mm). The tray was immediately placed in a chamber maintained at 22° C. Throughout the test, water was added to the soil whenever necessary to maintain its moisture content at the desired level. The emerging seedlings were counted each day until the maximum stand count had been reached. The warm germination test was carried out with the soil having a moisture content of 18, 21 or 29% (simulating dry soil, normal soil, and saturated soil conditions).

Temperature-Dependent Water Uptake Test

Two different germination paper sheets 10×15 in. (250×375 mm), available from Anchor Paper Co. under the tradenames Anchor #38 and Anchor #76, were used in each test. The dry sheets were soaked in water for about 30 minutes and then squeeze dried so that the wet sheets weighed about three times as much as the dried sheets. Two samples, each containing about 10 g of seeds, were withdrawn from a seed lot, and weighed. Each sample was spread uniformly on one of the wet Anchor #76 sheets, and then covered with a wet Anchor #38 sheet. Each pair of sheets was rolled up, secured with a rubber band, and sealed within a plastic bag. Each plastic bag was immediately placed in a chamber maintained at a controlled temperature, one at 10° C. and the other at 22° C. After 48 hours, the seeds were removed from the germination sheets and weighed. The ratio of the weight of the seeds maintained at 22° C. to the weight of the seeds maintained at 10° C. was designated the Water Uptake Switch Ratio. The test was repeated three times, and the results averaged.

Quality Control Water Uptake Test

Wet Anchor #38 and Anchor #76 germination sheets were prepared as in the Temperature-dependent Water Uptake Test. A sample containing about 10 g of seeds, was withdrawn from a seed lot and weighed. The sample was spread uniformly on one of the wet Anchor #76 sheets, and then covered with a wet Anchor #38 sheet. The sheets were rolled up, secured with a rubber band, and sealed within a plastic bag. The plastic bag was immediately placed in a chamber maintained at 22° C. or at 10° C. After 16 hours at 22° C., or after 48 hours at 10° C., the seeds were removed from the germination sheets and weighed. The test was conducted with three different samples, and the results averaged. The % water uptake after 16 hours at 22° C. was then used to estimate the water uptake at 22° C. for 48 hours, using earlier results in which the water uptake at 22° C. was measured at 16 and at 48 hours. We have found that the estimated water uptake at 22° C. for 48 hours in this test is preferably 20–24%, because the coated seed has a Heat Unit Delay of less than 50. We have also found that a water uptake of 8–10% after 48 hours at 10° C. in this test is desirable because this corresponds to a satisfactory result in the Vigor Test.

Examples 11–26

In Examples 11–26, which are summarized in Table 2 below, seeds from seed lot FC 8417 were used. In Example 11, the seeds were not given any further treatment. In Example 12, the seeds were given a coating of Formulation B (which did not contain any fungicide), applied by the "Polymer only Coating Method". In Examples 13–16, 18, 19, and 22, the seeds were given an undercoating of fungicides, in the amounts shown in Table 2, applied by the "Fungicide under Coating Method", followed by a coating of Formulation B (which did not contain any fungicide), applied by the "Polymer only Coating Method". In Examples 17, 19, 21 and 23–26, the seeds were given a coating of Formulation B to which had been added fungicides in the amounts shown in Table 2, applied by the "Fungicide in Polymer Coating Method". In each of Examples 10–26, the seeds were given a final coating of formulation H by the Overcoat Method. The seeds were then subjected to the Vigor Test and the Warm Germination Test.

Table 2 shows the coating formulations, with the location and quantities of Captan, Apron and Thiram (abbreviated to C, A and T) in grams per 10 lb (4.5 kg) of seed, and the results obtained. The figures given in parentheses, after the % germination in the Warm Germination tests, are the Heat Unit Delays in those tests. The negative Heat Unit Delay values show that the coated seeds in question emerged more rapidly than the uncoated seeds.

As Table 2 shows, under the test conditions of Examples 11–26, the untreated seeds (Example 11) show 0% germination in the Vigor (Cold Germination) Test. The seeds coated with only an SCC polymer, without any fungicide (Example 12), show germination of only 8% in the Vigor Test. When the fungicides were slurried onto the exterior of the seeds in the conventional way, without any polymer (Examples 13–16), the seeds showed germination of only 23–33% in the Vigor Test. However, when the fungicides were incorporated into Formulation B (containing a crystalline SCC polymer and an amorphous styrene-acrylic polymer), surprisingly good results were obtained in the Vigor Test.

As is shown by the results in Example 11, the seeds used in these experiments had very poor vigor. Such seeds were deliberately selected in order to study the effect on germination of the fungicides and the polymeric coatings.

TABLE 2

| Ex No | Coating C | A | T | Loc'n | Polymer | Vigor Test | Warm Germination (Heat Unit Delay) 18% H$_2$O | 21% H$_2$O | 29% H$_2$O |
|---|---|---|---|---|---|---|---|---|---|
| 11 | — | — | — | — | — | 0 | 69 (0) | 65 (0) | 48 (0) |
| 12 | — | — | — | — | Form. B | 8 | 68 (48) | 71 (54) | 42 (0) |
| 13 | 8.5 | 4.8 | — | under | None | 24 | 96 (4) | 98 (−7) | 85 (−9) |
| 14 | — | 4.8 | 9.0 | under | None | 23 | 96 (3) | 95 (−5) | 93 (−10) |
| 15 | 8.5 | — | 9.0 | under | None | 33 | 95 (3) | 99 (−7) | 90 (−8) |
| 16 | 8.5 | 4.8 | 9.0 | under | None | 23 | 94 (0) | 97 (−6) | 90 (−6) |
| 17 | — | 4.8 | — | in | Form. B | 5 | 71 (68) | 77 (60) | 34 (36) |
| 18 | — | 4.8 | — | under | Form. B | 21 | 88 (98) | 89 (85) | 47 (29) |
| 19 | — | — | 9.0 | in | Form. B | 60 | 96 (82) | 91 (61) | 79 (39) |
| 20 | — | — | 9.0 | under | Form. B | 58 | 93 (101) | 94 (93) | 81 (29) |
| 21 | 8.5 | — | — | in | Form. B | 81 | 81 (93) | 95 (90) | 66 (45) |
| 22 | 8.5 | — | — | under | Form. B | 63 | 90 (91) | 95 (92) | 68 (40) |
| 23 | 8.5 | 4.8 | — | in | Form. B | 70 | 85 (90) | 86 (88) | 86 (37) |
| 24 | — | 4.8 | 9.0 | in | Form. B | 61 | 94 (100) | 94 (88) | 88 (33) |
| 25 | 8.5 | — | 9.0 | in | Form. B | 77 | 96 (84) | 96 (75) | 90 (43) |
| 26 | 8.5 | 4.8 | 9.0 | in | Form. B | 67 | 97 (67) | 96 (84) | 92 (30) |

Examples 27–36

In Examples 27–36, which are summarized in Table 3 below, seeds from three different seed lots (FC8409, FC9304 and FC8083) were used. All the seeds had been pretreated, using commercially available fungicides, so that they were coated with Captan (300 ppm) and Apron (25 ppm). In Examples 27, 30 and 33, the seeds were not given any further treatment. In the other Examples, the seeds were coated with different coating formulations. In Examples 28, 29, 31, 32, and 34–36, the seeds were given an undercoating of Apron (50 ppm) applied by the "Fungicide under Coating Method". In Examples 28, 29, and 34–36, the undercoating was followed by a coating of Formulation B containing Captan (300 ppm) and Thiram (838 ppm), applied by the "Fungicide in Polymer Coating Method". In Examples 31 and 32, the undercoating was followed by a coating of Formulation C containing Captan (300 ppm) and Thiram (838 ppm), applied by the "Fungicide in Polymer Coating Method". In Examples 28, 29 and 34–36, the seeds were given a final coating of formulation H by the Overcoat Method. The seeds were then subjected to the Vigor Test and the Warm Germination Test at 22° C.

Table 3 shows the coating formulations, with the location and quantities in ppm of the fungicides, and the results obtained. As can be seen from Table 3, when the fungicides were incorporated into a polymeric coating comprising a crystalline SCC polymer and an amorphous polymer, improved results were obtained in the Vigor (Cold Germination) test.

TABLE 3

| Ex. No. | Seed Lot | Coating C | A | T | Loc'n | Polymer | Vigor test | Warm Germ. |
|---|---|---|---|---|---|---|---|---|
| 27 | FC8409 | 300 | 25 | — | — | none | 63 | 96 |
| 28 | FC8409 | 300 + 300 | 25 + 50 | — 838 | under in | Form B | 96 | 98 |
| 29 | FC8409 | 300 + 300 | 25 + 50 | — 838 | under in | Form B | 93 | 98 |
| 30 | FC9307 | 300 | 25 | — | under | none | 41 | 95 |
| 31 | FC9307 | 300 + 300 | 25 + 50 | — 838 | under in | Form C | 68 | 94 |
| 32 | FC9307 | 300 + 300 | 25 + 50 | — 838 | under in | Form C | 67 | 97 |
| 33 | FC8083 | 300 | 25 | — | — | none | 74 | |
| 34 | FC8083 | 300 + 300 | 25 + 50 | — 838 | under in | Form B | 94 | |
| 35 | FC8083 | 300 + 300 | 25 + 50 | — 838 | under in | Form B | 95 | |
| 36 | FC8083 | 300 + 300 | 25 + 50 | — 838 | under in | Form B | 92 | |

Examples 37–41

In Examples 37–41, which are summarized in Table 4 below, seeds from same seed lot (FC8417) were used. All the seeds had been pretreated, using commercially available fungicides, so that they were coated with Captan (300 ppm) and Apron (25 ppm). In Example 37, the seeds were not given any further treatment. In Examples 38–41, the seeds were first given an undercoating of Apron (50 ppm) applied by the "Fungicide under Coating Method". The seeds were then coated with different coating formulations, as specified in Table 4, containing Captan (300 ppm) and Thiram (838 ppm), by a method similar to the Fungicide in Polymer Coating Method but using the ETS R-12 coater. In Examples 38 and 39, amorphous polymers were applied as 35% solutions. Finally, the seeds were given a coating of Formulation H by the Overcoat Method. The seeds were then subjected to the Vigor Test and the Warm Germination Test at 22° C.

Table 4 shows the coating formulations, with the location and quantities of Captan, Apron and Thiram (abbreviated to C, A and T) in ppm, and the results obtained. The figures given in parentheses, after the % germination in the Warm Germination tests, are the Heat Unit Delays in those tests.

FIGS. 1 and 2 show the rate at which the seedlings emerged in the Vigor Tests and the Warm Germination Tests.

TABLE 4

| Ex. No. | Coating | | | | | Vigor test | Warm Germ. (Heat Unit Delay) |
|---|---|---|---|---|---|---|---|
| | C | A | T | Loc'n | Polymer | | |
| 37 | 300 | 25 | — | — | None | 26 | 99 (0) |
| 38 | 300 + 300 | 25 + 50 | — 838 | under in | Rhoplex SG20 | 81 | 98 (117) |
| 39 | 300 + 300 | 25 + 50 | — 838 | under in | Flexthane 620 | 65 | 94 (174) |
| 40 | 300 + 300 | 25 + 50 | — 838 | under in | Formulation C | 69 | 99 (84) |
| 41 | 300 + 300 | 25 + 50 | — 838 | under in | Formulation C | 56 | 99 (32) |

Examples 42–53

In Examples 42–53, which are summarized in Table 5 below, seeds from two different seed lots (FC 8409 and FC9307) were used. All the seeds had been pretreated, using commercially available fungicides, so that they were coated with Captan (300 ppm) and Apron (25 ppm). In Example 42 and 48, the seeds were not given any further fungicide treatment. In Examples 43 and 49, the seeds were given a coating of Apron (25 ppm), Captan (300 ppm) and Thiram (838 ppm), applied by the Fungicide Only Coating Method. In Examples 44–47 and 50–53, the seeds were first given an undercoating of Apron (50 ppm) applied by the "Fungicide Only Coating Method", and were then coated with Formulation B containing Captan (300 ppm) and Thiram (838 ppm), by the Fungicide in Polymer Coating Method. All the seeds were given a final coating of Formulation H by the Overcoat Method. The seeds were then subjected to the Vigor Test.

Table 5 shows the coating formulations, with the location and quantities of Captan, Apron and Thiram (abbreviated to C, A and T) in ppm, and the results obtained.

TABLE 5

| Ex. No. | Seed Lot | Coating Formulation | | | | | Vigor Test |
|---|---|---|---|---|---|---|---|
| | | C | A | T | Loc'n | Polymer | |
| 42 | FC8409 | 300 | 25 | — | — | None | 62 |
| 43 | FC8409 | 300 + 300 | 25 + 50 | 838 | — | None | 64 |
| 44 | FC8409 | 300 + 300 | 25 + 50 | — | under 838 in | Form B | 90 |
| 45 | FC8409 | 300 + 300 | 25 + 50 | — | under 838 in | Form B | 84 |
| 46 | FC8409 | 300 + 300 | 25 + 50 | — | under 838 in | Form B | 88 |
| 47 | FC8409 | 300 + 300 | 25 + 50 | — | under 838 in | Form B | 86 |
| 48 | FC9307 | 300 | 25 | — | — | None | 0 |
| 49 | FC9307 | 300 + 300 | 25 + 50 | 838 | — | None | 68 |
| 50 | FC9307 | 300 + 300 | 25 + 50 | — | under 838 in | Form B | 93 |
| 51 | FC9307 | 300 + 300 | 25 + 50 | — | under 838 in | Form B | 97 |
| 52 | FC9307 | 300 + 300 | 25 + 50 | — | under 838 in | Form B | 99 |
| 53 | FC9307 | 300 + 300 | 25 + 50 | — | under 838 in | Form B | 96 |

Examples 54–60

In Examples 54–60, which are summarized in Table 6 below, seeds from two different seed lots (FC 8288 and FC9301) were used. All the seeds had been pretreated, using commercially available fungicides, so that they were coated with Captan (300 ppm) and Apron (25 ppm). In Examples 54 and 57, the seeds were not given any further treatment. In Examples 55, 56 and 58–60, the seeds were first given an undercoating of Apron (50 ppm) applied by the "Fungicide Only Coating Method", and were then coated with Formulation C containing Captan (300 ppm) and Thiram (838 ppm), by a method similar to the Fungicide in Polymer Coating Method but using the ETS R-12 coater. The seeds were then subjected to the Vigor Test.

Table 6 shows the coating formulations, with the location and quantities of Captan, Apron and Thiram (abbreviated to C, A and T) in ppm, and the results obtained. As can be seen from Table 6, improved results were obtained with both of these high vigor seeds—FC8409 and FC9307—when the fungicides were incorporated into a polymeric coating containing an SCC polymer and an amorphous polymer. From

TABLE 6

| Ex. No. | Seed Lot | Coating Formulation | | | | | Vigor Test |
|---|---|---|---|---|---|---|---|
| | | C | A | T | Loc'n | Polymer | |
| 54 | FC8288 | 300 | 25 | — | — | None | 78 |
| 55 | FC8288 | 300 + 300 | 25 + 50 | — | under 838 in | Form B | 98 |
| 56 | FC8288 | 300 + 300 | 25 + 50 | — | under 838 in | Form B | 96 |
| 57 | FC9301 | 300 | 25 | — | — | None | 82 |
| 58 | FC9301 | 300 + 300 | 25 + 50 | — | under 838 in | Form B | 82 |
| 59 | FC9301 | 300 + 300 | 25 + 50 | — | under 838 in | Form B | 96 |
| 60 | FC9301 | 300 + 300 | 25 + 50 | — | under 838 in | Form B | 100 |

Examples 61–67

In Examples 61–67, which are summarized in Table 7 below, seeds from same seed lot (FC 8809) were used. All the seeds had been pretreated, using commercially available fungicides, so that they were coated with Captan (300 ppm) and Apron (25 ppm). In Example 61, the seeds were not given any further treatment. In Examples 62–67, the seeds were first given an undercoating of Apron (50 ppm) applied by the "Fungicide Only Coating Method", and were then coated with Formulation C containing Captan (300 ppm) and Thiram (838 ppm), and, in Examples 63–67, the indicated amounts of Gaucho 600, by a method similar to the Fungicide in Polymer Coating Method but using the ETS R-12 coater. The seeds were planted in field trials in Missouri.

Table 7 shows the coating formulations, with the location and quantities in ppm of Captan, Apron, Thiram and Gaucho 600 (abbreviated to C, A, T and G respectively), and the results obtained, in particular the "emergence" and the % infection by seed corn maggot infestation. Emergence is the percentage of the total seeds planted that emerge in a given plot or test sample.

TABLE 7

| Ex No | Seed Lot | Coating | | | | | Polymer | Emergence | % infection |
|---|---|---|---|---|---|---|---|---|---|
| | | C | A | T | G | Loc'n | | | |
| 61 | FC8809 | 300 | 25 | — | — | — | None | 34 | 55 |
| 62 | FC8809 | 300 + 300 | 25 + 50 | — | 838 | under in | Form C | 40 | 15 |
| 63 | FC8809 | 300 + 300 | 25 + 50 | — | 860 838 | under in | Form C | 36 | 22 |
| 64 | FC8809 | 300 + 300 | 25 + 50 | — | 8900 838 | under in | Form C | 37 | 20 |
| 65 | FC8809 | 300 + 300 | 25 + 50 | — | 860 838 | under in | Form C | 40 | 10 |
| 66 | FC8809 | 300 + 300 | 25 + 50 | — | 4400 838 | under in | Form C | 41 | 8 |
| 67 | FC8809 | 300 + 300 | 25 + 50 | — | 8900 838 | under in | Form C | 35 | 2 |

Examples 68–71

In Examples 68–71, which are summarized in Table 8 below, seeds from same seed lot (FC 8417) were used. In Examples 68, a mixture of Captan, Apron, Thiram and Lorsban was coated on the seeds using the Fungicide Only Coating Method. In Examples 69–71, the seeds were coated with Formulation B containing Captan, Apron and Thiram (Ex. 69) or Lorsban Captan, Apron, Thiram and Lorsban (Examples 70 and 71) by the Fungicide in Polymer Coating Method. Finally, the seeds were given a coating of Formulation H by the Overcoat Method. Representative coated seeds were then subjected to the Vigor Test, and the Warm Germination Test at 22° C.

Table 8 shows the coating formulations, with the location and quantities (in grams per kilogram of seeds) of Captan, Apron, Thiram and Lorsban (abbreviated to C, A, T and L respectively), and the results obtained. As can be seen from Table 8, improved results were obtained in the Vigor test when the fungicide and insecticide where incorporated into a polymeric coating comprising an SCC polymer and an amorphous polymer.

TABLE 8

| Ex No | Coating | | | | | Polymer | Vigor Test | Warm Germ. |
|---|---|---|---|---|---|---|---|---|
| | C | A | T | L | Loc'n | | | |
| 68 | 8.5 | 4.8 | 9.0 | 8.7 | — | — | 35 | 92 |
| 69 | 8.5 | 4.8 | 9.0 | 0 | in | Form B | 71 | 95 |
| 70 | 8.5 | 4.8 | 9.0 | 8.7 | under | Form B | 87 | 94 |
| 71 | 8.5 | 4.8 | 9.0 | 8.7 | in | Form B | 74 | 94 |

Table 9 below shows the maximum elongation and tensile strength (in grams) at different temperatures of the SCC polymers C3-A and D3-J, the amorphous polymers Rhoplex SG 20 and Optive S-100, and various blends thereof.

TABLE 9

| | | | | 12° C. | | 18° C. | |
|---|---|---|---|---|---|---|---|
| % C3-A | % D3-J | % SG20 | % S-100 | % elong | tensile | % elong | tensile |
| 100 | | | | 60 | 1250 | 170 | 365 |
| 70 | | 30 | | 133 | 3560 | 188 | 1370 |
| 70 | | | 30 | | | 137 | 1180 |
| | 100 | | | 150 | 475 | 250 | 100 |
| | 60 | 40 | | 114 | 3400 | 202 | 900 |
| | | 100 | | | | 149 | 3000 |
| | | | 100 | | | 179 | 3360 |

We claim:
1. A method of
(A) testing a seed lot in which the seeds are fungicide-treated seeds, the test method comprising
   (1) withdrawing a representative sample of seeds from the seed lot;
   (2) placing the seeds of the representative sample at a depth of 1 to 1.5 inch in soil which has a moisture content of M %, where M is 21 to 25 and is substantially constant;
   (3) maintaining the soil and the seeds therein at a temperature of 3 to 7° C. for 19 to 24 days;
   (4) immediately after step (3), maintaining the soil and the seeds therein at a temperature of 20 to 25° C., while maintaining the moisture content of the soil at L %, where L is the same as M; and
   (5) determining that the percentage of the seeds which have developed into seedlings on the day on which a maximum number of seedlings can be observed is at least 75%; and
(B) forming a continuous polymeric coating on the remaining seeds in the seed lot, the continuous polymeric coating comprising
   (1) a polymeric component which comprises
      (a) at least one side chain crystalline (SCC) polymer which has a peak melting temperature $T_p$ of 0 to 40° C., an onset of melting temperature $T_o$ such that $(T_p-T_o)$ is less than 10° C., and a heat of fusion of at least 5 J/g, and
(b) at least one amorphous polymer having a $T_g$ of at least 20° C.; and
(2) a fungicidal component comprising
(a) a contact fungicide, and
(b) a systemic fungicide.

2. A method according to claim 1 wherein, in the test method, the seeds of the representative sample are placed in the soil at a depth of about 1.25 inch; M is about 23; L is about 23; in step (3), the soil and the seeds therein are maintained a temperature of about 5° C. for about 21 days; and in step (4), the soil and the seeds therein are maintained a temperature of about 22° C.

3. A method according to claim 1 wherein the percentage determined in step (5) is at least 85%.

4. A method according to claim 1 wherein the seeds prepared in step (B) have a Heat Unit Delay of less than 50.

5. A method according to claim 1 wherein the percentage determined in step (5) of the test method is at least 95%.

6. A method of
(A) testing a seed lot in which the seeds are fungicide-treated hybrid corn seeds, the test method comprising
(1) withdrawing a representative sample of seeds from the seed lot;
(2) placing the seeds of the representative sample at a depth of 1 to 1.5 inch in soil which has a moisture content of M %, where M is 21 to 25 and is substantially constant;
(3) maintaining the soil and the seeds therein at a temperature of 3 to 7° C. for 19 to 24 days;
(4) immediately after step (3), maintaining the soil and the seeds therein at a temperature of 20 to 25° C., while maintaining the moisture content of the soil at L %, where L is the same as M; and
(5) determining that the percentage of the seeds which have developed into seedlings on the day on which a maximum number of seedlings can be observed is at least 85%; and
(B) forming a continuous polymeric coating on the remaining seeds in the seed lot, the continuous polymeric coating comprising
(1) a polymeric component which comprises
(a) at least one side chain crystalline (SCC) polymer which has a peak melting temperature $T_p$ of 0 to 40° C., an onset of melting temperature $T_o$ such that $(T_p-T_o)$ is less than 10° C., and a heat of fusion of at least 5 J/g, and
(b) at least one amorphous polymer having a $T_g$ of at least 20° C.; and
(2) a fungicidal component comprising
(a) a contact fungicide, and
(b) a systemic fungicide.

7. A method of
(A) testing a seed lot in which the seeds are fungicide-treated hybrid corn seeds, the test method comprising
(1) withdrawing a representative sample of seeds from the seed lot;
(2) placing the seeds of the representative sample at a depth of 1 to 1.5 inch in soil which has a moisture content of M %, where M is 21 to 25 and is substantially constant;
(3) maintaining the soil and the seeds therein at a temperature of 3 to 7° C. for 19 to 24 days;
(4) immediately after step (3), maintaining the soil and the seeds therein at a temperature of 20 to 25° C., while maintaining the moisture content of the soil at L %, where L is the same as M; and
(5) determining that the percentage of the seeds which have developed into seedlings on the day on which a maximum number of seedlings can be observed is at least 85%; and
(B) forming a continuous polymeric coating on the remaining seeds in the seed lot, the continuous polymeric coating comprising
(1) a polymeric component which comprises
(a) 30 to 95% of at least one crosslinked side chain crystalline (SCC) polymer which has a peak melting temperature $T_p$ of 0 to 40° C., an onset of melting temperature $T_o$ such that $(T_p-T_o)$ is less than 10° C., and a heat of fusion of at least 15 J/g, and
(b) 70 to 5% of at least one amorphous polymer having a $T_g$ of −60 to 40° C.; and
(2) a fungicidal component which comprises
(a) a contact fungicide; and
(b) a systemic fungicide.

8. A method according to claim 6 wherein the polymeric coating further comprises at least one amorphous polymer having a $T_g$ of −60 to 40° C.

9. A method according to claim 6 wherein the seeds prepared in step (B) have a Heat Unit Delay of less than 50.

10. A method of growing crops which comprises planting the coated seeds prepared in step (B) of a method as defined in claim 1.

11. A method of growing crops which comprises planting the coated corn seeds prepared in step (B) of a method as defined in claim 6, the corn seeds being planted in soil which is substantially the same as the soil used in step (A).

12. A method according to claim 11 which includes harvesting corn from the plants produced by the planted corn seeds.

13. A method according to claim 10 wherein the seeds are planted in soil which is substantially the same as the soil used in step (A).

14. A method according to claim 10 which includes harvesting the crops from the plants produced by the planted seeds.

15. A method of processing a seed lot in which the seeds are fungicide-treated seeds, the method comprising
(1) withdrawing a representative sample of seeds from the seed lot;
(2) placing the seeds of the representative sample at a depth of 1 to 1.5 inch in soil which has a moisture content of M %, where M is 21 to 25 and is substantially constant;
(3) maintaining the soil and the seeds therein at a temperature of 3 to 7° C. for 19 to 24 days;
(4) immediately after step (3), maintaining the soil and the seeds therein at a temperature of 20 to 25° C., while maintaining the moisture content of the soil at L %, where L is 21 to 25 and is substantially constant; and
(5) determining the percentage of the seeds which have developed into seedlings X days after the beginning of step (4), where X is 7 to 28.

16. A method according to claim 15 wherein the seeds of the representative sample are placed in the soil at a depth of about 1.25 inch; M is about 23; L is about 23; in step (3), the soil and the seeds therein are maintained a temperature of about 5° C. for about 21 days; and in step (4), the soil and the seeds therein are maintained a temperature of about 22° C.

17. A method according to claim 15 wherein, if the percentage determined in step (5) is greater than 75%, the method further comprises
  (6) forming a continuous polymeric coating on the remaining seeds in the seed lot, the continuous polymeric coating comprising
    (i) a polymeric component which comprises
      (a) at least one side chain crystalline (SCC) polymer which has a peak melting temperature $T_p$ of 0 to 40° C., an onset of melting temperature $T_o$ such that $(T_p-T_o)$ is less than 10° C., and a heat of fusion of at least 5 J/g, and
      (b) at least one amorphous polymer having a $T_g$ of at least 20° C.; and
    (ii) a fungicidal component comprising
      (a) a contact fungicide, and
      (b) a systemic fungicide.

18. A method according to claim 15 wherein, in step (5), the percentage which is determined is the percentage of the seeds which have developed into seedlings on the day on which a maximum number of seedlings can be observed; and if said percentage is greater than 85%, the method further comprises
  (6) forming a continuous polymeric coating on the remaining seeds in the seed lot, the continuous polymeric coating comprising
    (i) a polymeric component which comprises
      (a) at least one side chain crystalline (SCC) polymer which has a peak melting temperature $T_p$ of 0 to 40° C., an onset of melting temperature $T_o$ such that $(T_p-T_o)$ is less than 10° C., and a heat of fusion of at least 5 J/g, and
      (b) at least one amorphous polymer having a $T_g$ of at least 20° C.; and
    (ii) a fungicidal component comprising
      (a) a contact fungicide, and
      (b) a systemic fungicide.

19. A method according to claim 18 wherein the seeds prepared in step (6) have a Heat Unit Delay of less than 50.

20. A method according to claim 18 wherein the percentage determined in step (5) is at least 95%.

* * * * *